United States Patent [19]

Sundhar

[11] Patent Number: 5,209,238
[45] Date of Patent: May 11, 1993

[54] ELECTRONIC OVULATION MONITOR

[76] Inventor: Shaam P. Sundhar, 87 Juniper Ave., Westerville, Ohio 43081

[21] Appl. No.: 878,683

[22] Filed: May 5, 1992

Related U.S. Application Data

[63] Continuation-in-part of Ser. No. 649,213, Jan. 25, 1991, which is a continuation of Ser. No. 395,002, Aug. 17, 1989, abandoned.

[51] Int. Cl.⁵ .............................................. A61B 10/00
[52] U.S. Cl. ................................. 128/738; 364/413.12; 128/754
[58] Field of Search ............... 128/738, 778, 788, 899, 128/734; 606/119; 364/413.12

[56] References Cited

U.S. PATENT DOCUMENTS

| | | | |
|---|---|---|---|
| 2,945,491 | 7/1960 | Gibbs | 128/738 |
| 4,443,851 | 4/1984 | Lin | 128/738 |
| 4,465,077 | 8/1984 | Schneider | 128/738 |
| 4,498,481 | 2/1985 | Lemke | 128/734 |
| 4,752,880 | 6/1988 | Aeschlimann | 364/413.12 |
| 4,753,247 | 6/1988 | Kirsner | 128/738 |

Primary Examiner—Peter A. Aschenbrenner
Attorney, Agent, or Firm—Biebel & French

[57] ABSTRACT

An electronic ovulation monitor is provided having a housing containing means for processing information, means which serve as a sensor to detect then transmit information to the means for processing of such information, and means for indicating the presence of a viable egg. The information which is processed includes values associated with mucous density, basal body temperature, pH level, and LH level. The information is processed and compared with data associated with the presence of a viable egg, such that if a viable egg is empirically indicated as being present, a visual display and audible component will signal such presence.

13 Claims, 11 Drawing Sheets

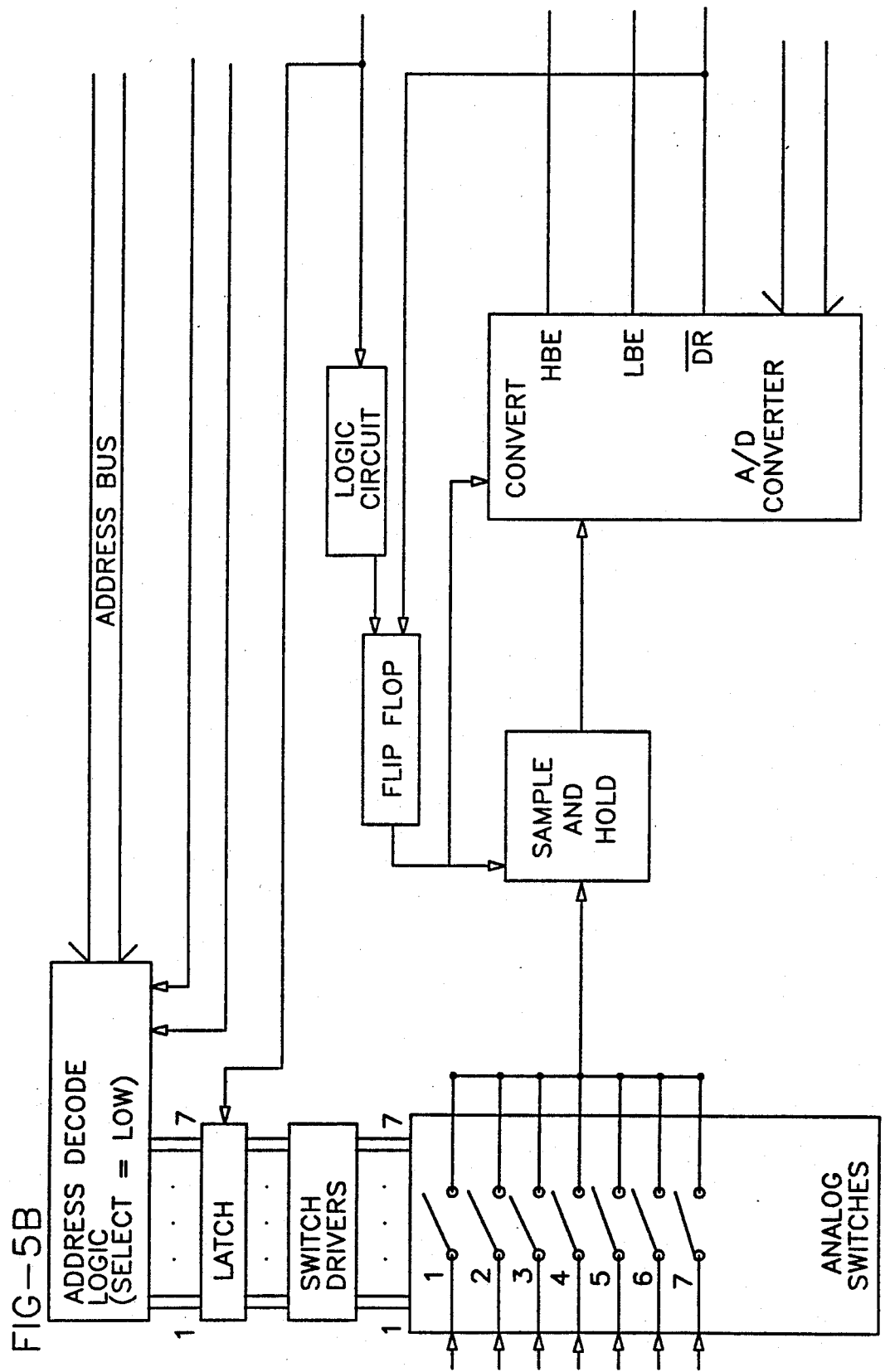

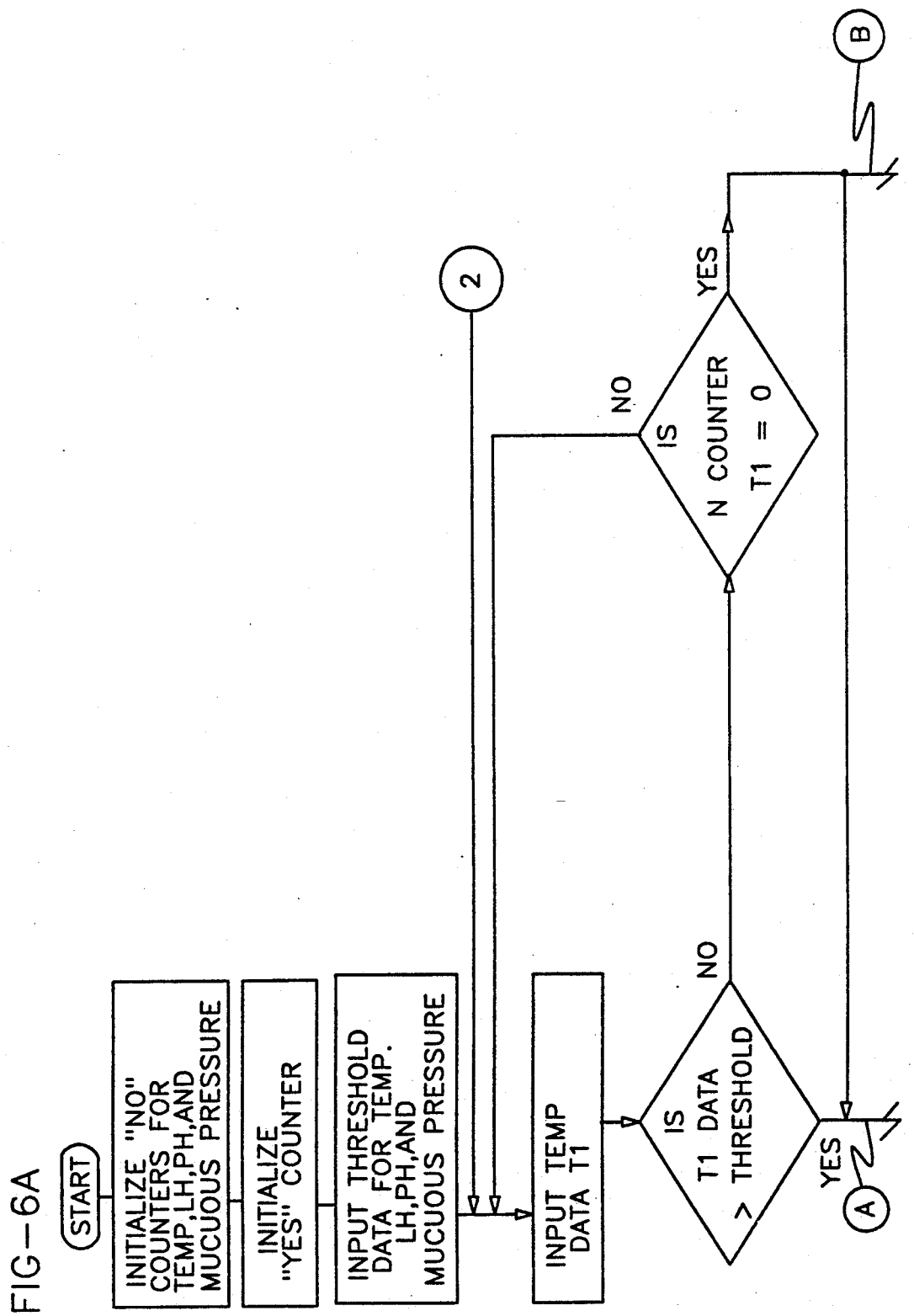

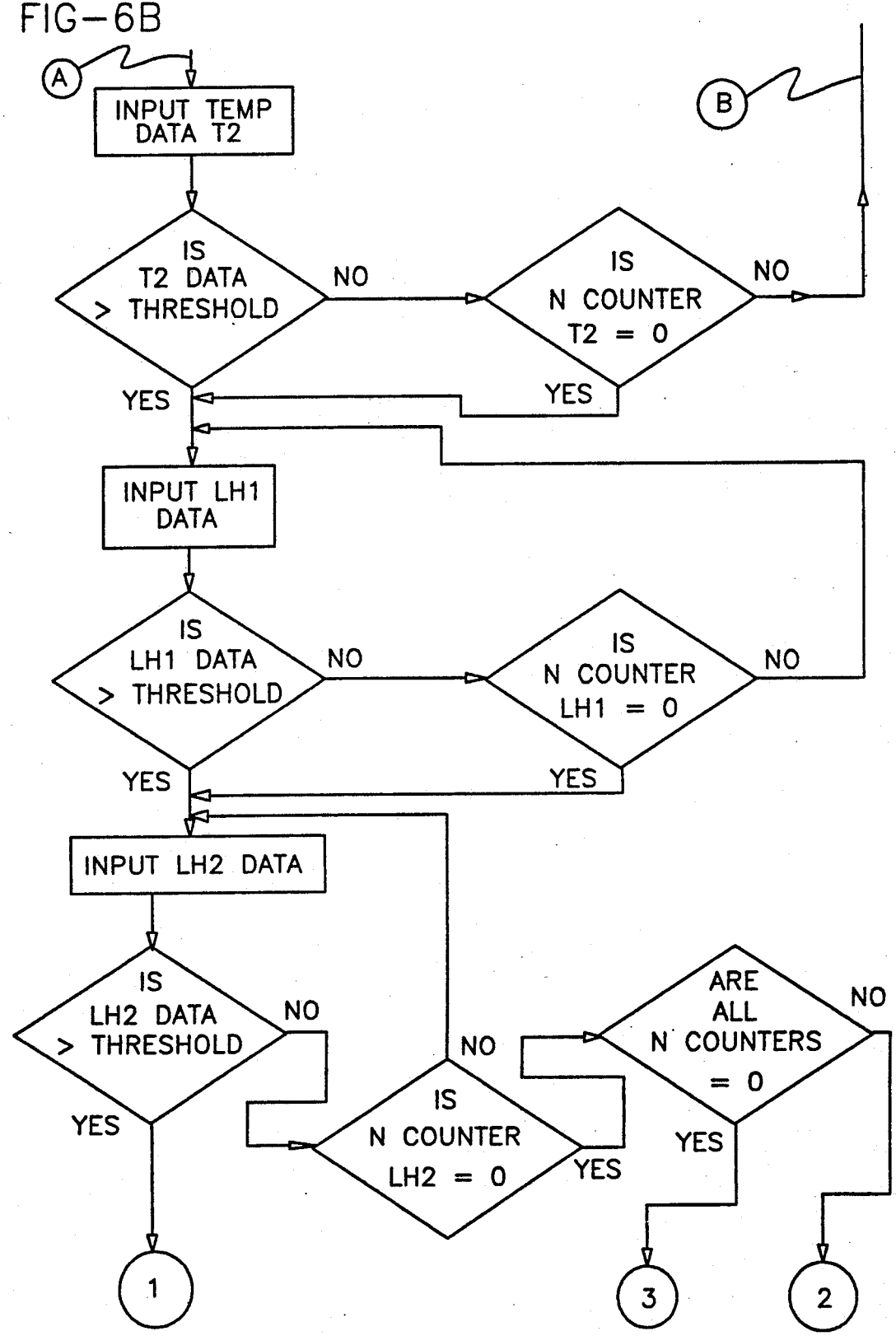

ELECTRONIC OVULATION MONITOR

This application is a continuation-in-part of Ser. No. 649,213 filed Jan. 25, 1991, which was a continuation of Ser. No. 395,002 filed Aug. 17, 1989 now abandoned.

BACKGROUND OF THE INVENTION

The present invention relates generally to a monitor, and more particularly, to a device for electronically sensing that ovulation has occurred.

Infertility and birth control superficially have nothing in common. Couples who have problems with infertility need to maximize fertilization of a viable egg. Meanwhile, other couples are desirous of intercourse absent the possibility of conception.

For couples suffering from infertility, it is extremely important for them to determine when ovulation has occurred, to maximize the potential for pregnancy. At ovulation, an egg is released from the ovary. This egg remains viable approximately 12-24 hours. Conception occurs when an egg present in the fallopian tube is fertilized by a sperm. However, the egg is present in the fallopian tube typically for only a few hours, i.e. 3-10. Meanwhile, sperm remains viable in a female for up to 48 hours. Thus, if a woman wishes to become pregnant it is necessary for the sperm and egg to interact within the 12-24 hours following ovulation.

Meanwhile, for other couples who desire to practice family planning or minimize the potential for pregnancy by monitoring the female ovulation cycle, it is possible to determine that portion of the month where conception is physically impossible. Thus, both infertility and birth control may be impacted by the ovulation cycle.

There are tests which can be conducted relative to the time of ovulation. For example, one test is designed to predict ovulation by comparing the pH in a woman's saliva with that of her vagina over the course of time. By comparing the changes in the pH levels of a woman's body, it is scientifically possible to predict when ovulation will occur. Such a test employs a device similar to the digital pH meters known to exist which permit a determination on the precise pH of a solution. Similarly, tests exist for measuring the level of luteinizing hormone. These tests can either include a urine test or a blood test. Luteinizing hormone is a hormone of protein-carbohydrate composition that is obtained from the interior lobe of the pituitary gland, and that in the female, stimulates the development of corpora lutea, and together with follicle stimulating hormone, the secretion of progesterone. The luteinizing hormonal level surges just before ovulation and drops after ovulation.

It is also possible to predict when ovulation has occurred based on the fact that the basal body temperature increases up to 1° F. Still a fourth test involves "ferning" of the cervical mucous. The optimal time for conception exists when the cervical mucous is at its maximum density. Presently medical personnel, in conjunction with a pelvic exam, can mircorscopically examine mucous which has been deposited on a slide. Whereas the normal amount of "ferning" ranges from 1-3, optimal conditions for conception exist when the value associated with "ferning" is 4+.

Attempting to conduct all of the above tests is both time consuming, relatively expensive, and requires the assistance of medical professionals. However, to verify that optimum conditions exist, all of the above tests should be performed and should test positive.

It is thus apparent that the need exists for an improved ovulation monitor which permits simple and quick establishment of whether ovulation has occurred.

SUMMARY OF THE INVENTION

The problems associated with prior ovulation monitoring kits and tests are overcome in accordance with the present invention by providing an electronic ovulation monitor comprising a housing having contained therein a power source, an audible component, a light emitting diode, and a micro-processor, with the micro-processor connected to a sensor located external the housing. The micro-processor measures the basal body temperature, mucous density, pH level and LH level. The monitor housing is substantially rod-shaped, having a first end and a second end. The base of the housing is located at the first end, and the sensor is located at the second end.

There is also disclosed an ovulation monitor having a housing which contains means for processing information, means which serve as a sensor to transmit information to the means for processing information, and a monitor having means for indicating the presence of a viable egg. The information includes basal body temperature, density of mucous, pH level and LH level. The means for indicating the presence of a viable egg includes an audible component and a visual component. The means for processing the information includes at least one micro-chip. The information is processed and compared with data associated with the presence of a viable egg, such that if a viable egg is empirically indicated as being present, then the means for indicating the presence of a viable egg will indicate such presence.

It is a primary object of the present invention to provide an electronic ovulation monitor which is simple and convenient to use and which results in a quick and effective determination of whether a viable egg is present.

Other objects and advantages of the invention will be apparent from the following description, the accompanying drawings and the appended claims.

DETAILED DESCRIPTION OF THE INVENTION

Figure 1:
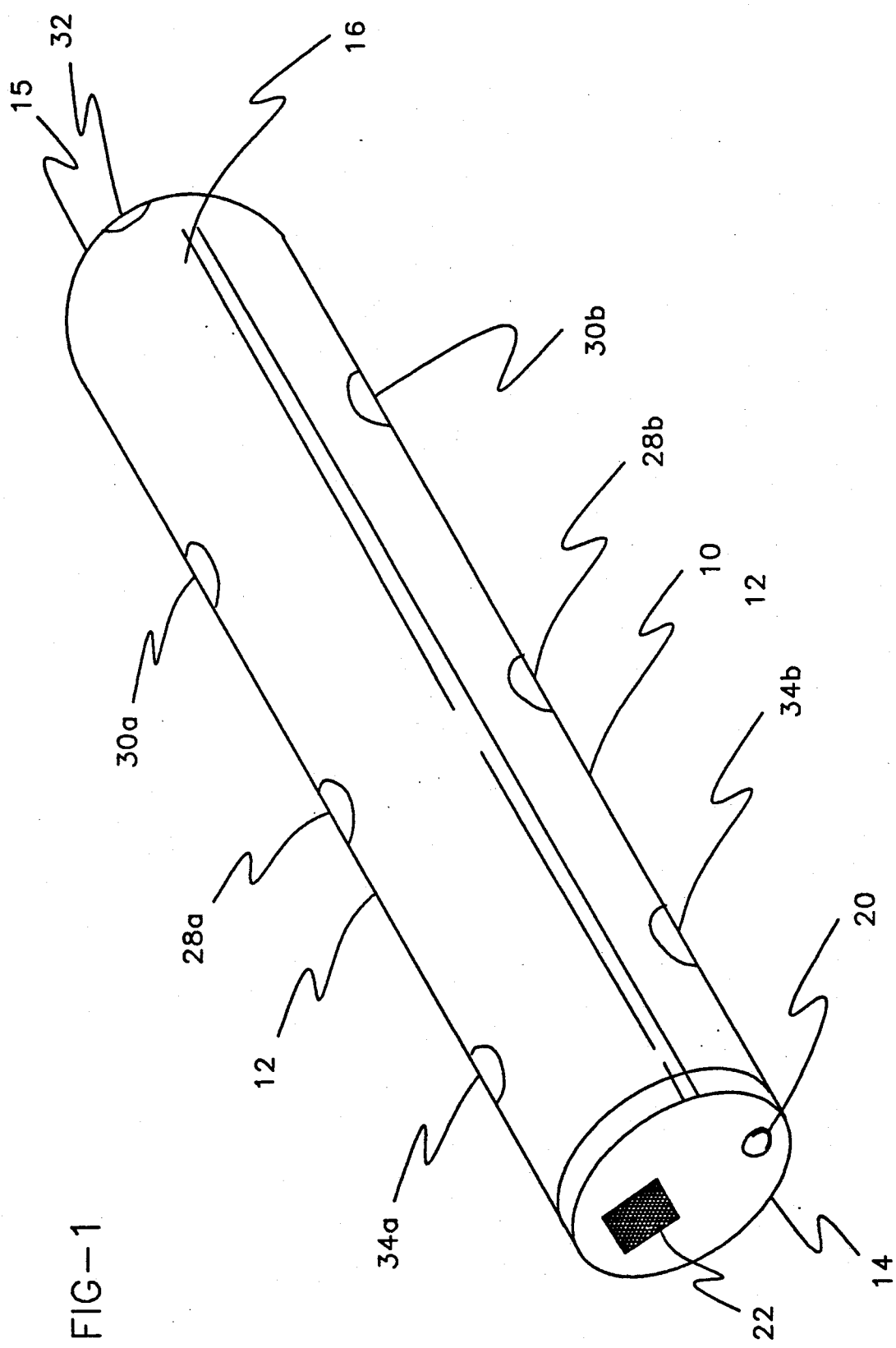
FIG. 1 is a perspective view of an electronic ovulation monitor in accordance with the present invention.

FIG. 1 is a perspective view of an electronic ovulation monitor made in accordance with the present invention and designated generally by the numeral 10. As can be seen, the ovulation monitor is comprised of a cylindrical tube 12 with a base 14 at its first end and a rounded second end 15. The external portion of the tube 15 includes sensing means 16. Sensing means 16 is shown as a plurality of sensors, although a unitary sensor unit having a plurality of sensors could be placed there. Preferably, the tube 12 has its housing formed from stainless steel approximately 1" in diameter and approximately 6" long.

Figure 2:
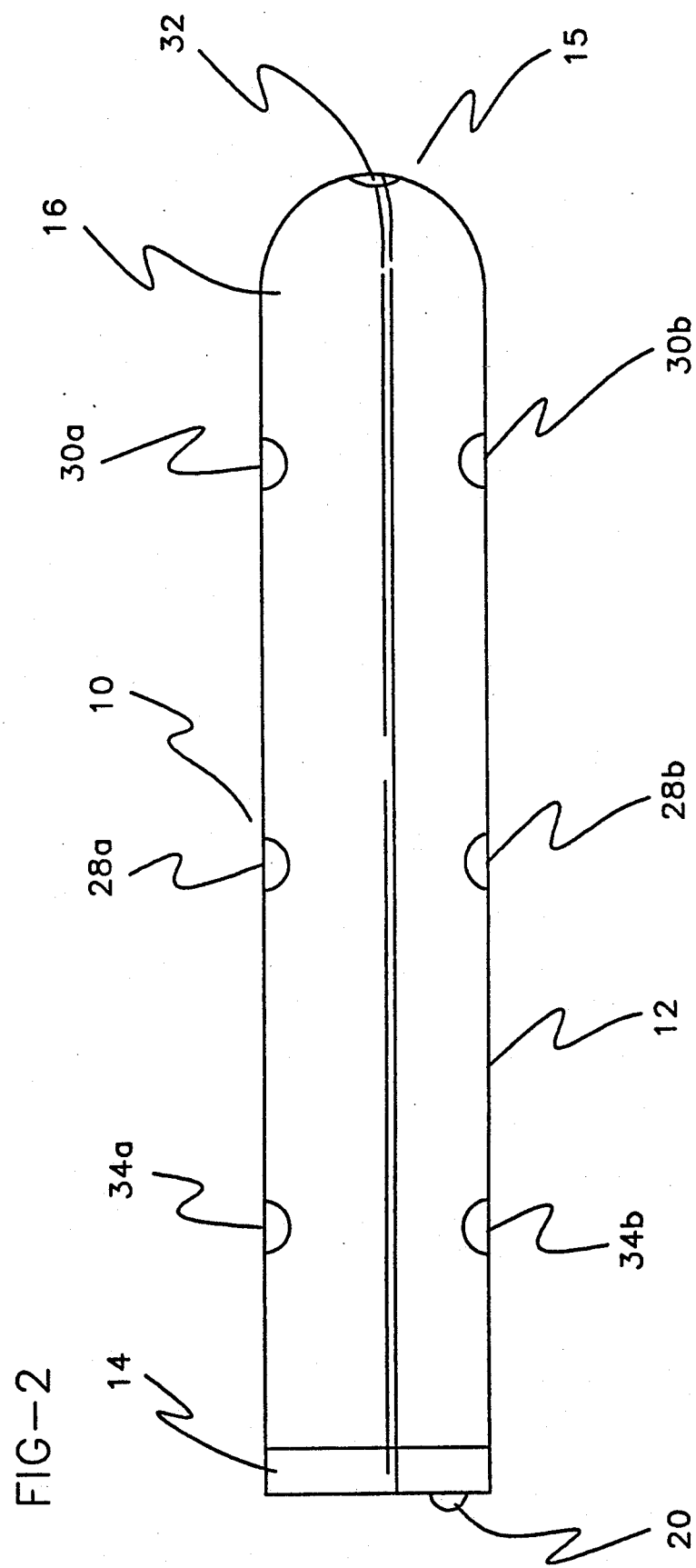
FIG. 2 is a side plan view of the monitor shown in FIG. 1.

As can be seen in FIGS. 1 and 2, base 14 is preferably screwed onto the substantially rod-shaped housing of the monitor and has affixed thereto a visual display 20 and an audible component 22. Preferably the visual display 20 is in the form of a light emitting diode, while the audible component is similar to that found in digital wristwatch alarms. The housing preferably has seven small holes drilled therethrough and has attached at those points fixed sensors to sense the basal body temperature, the pH level, the LH level, and the density of mucous in the vaginal canal and in the mouth of the cervix. Preferably the mucous sensor 22 is located at the tip of the housing to detect the presence at the mouth of the cervix once the housing is inserted in the vagina. Preferably, the other sensors are spread around the housing so that they can touch the vaginal muscles properly.

Figure 3:
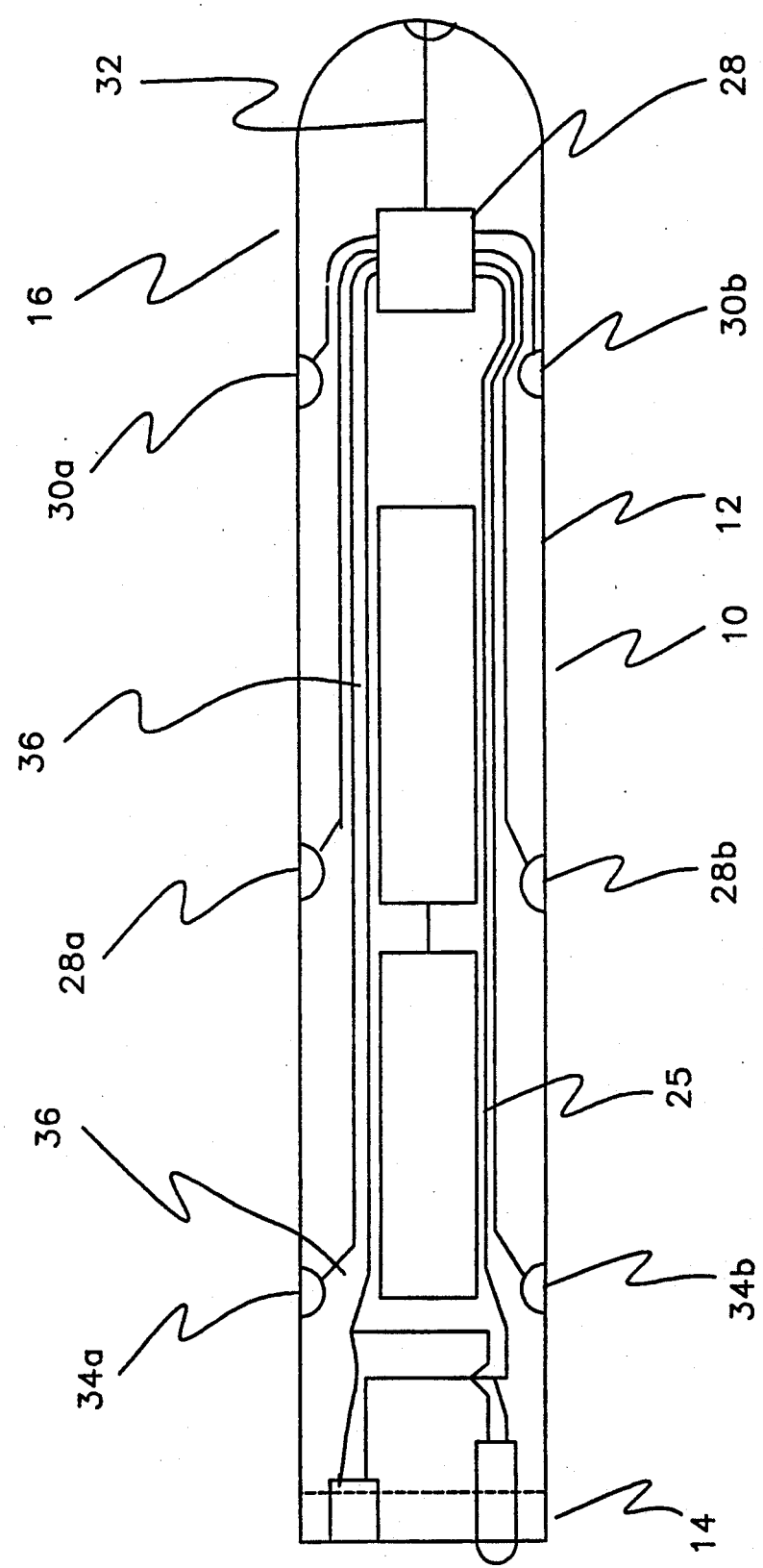
FIG. 3 is a schematic view showing the major components of the monitor of FIG. 1.

As best shown in FIG. 3, the housing contains visual display 20 and audible component 22 as well as a processing means 28 and power source 36. The circuitry 25 connects the components in a manner well known in the prior art of electronics. The processing means 28 preferably utilizes at least one micro-chip, however, a plurality of chips could be utilized with each chip dedicated to a single sensor. The micro-processor measure the basal body temperature, the mucous density, the pH level and the LH level with measuring means 30-33 respectively. The micro-processor serves as a means for processing information obtained by the measuring means, with the information obtained from the sensing means transmitted to the means for processing the information.

The processing means 28 contains data associated with the viscosity or thickness of mucous, basal body temperature, pH level and LH level as these values relate to ovulation. The sensing means permits the information obtained from such sensing means to be compared with the aforementioned data, such that changes to a thicker mucous, increased basal body temperature of at least 0.15° to 1° F., increased LH level, and change in pH level would be contra-indicative of the presence of a viable egg. If each of the four values registers the expected change, the presence of a viable egg is empirically indicated.

At such time as the processing means determines that the four factors indicating ovulation has recently occurred, the visual display 20 and audible component 22 will be activated. Preferably a small red light will flash, accompanied by a series of "beeps". This signals that the woman is able to conceive.

The various sensors associated with sensing means 16 include sensing units capable of determining the level of luteinizing hormone, the pH level, the basal body temperature, and the relative density or thickness of mucous based upon the emission of sound waves, similar to sonar. These types of sensors are discussed below.

In the housing, there are preferably two sensors that detect the instantaneous temperature of the vaginal muscles whenever the probe is inserted in the vagina. One of the prior art methods of determining whether or not ovulation has occurred, is to test for the elevation in body temperature during a woman's fertility cycle. Secretion of progesterone during the latter half of the cycle raises the body temperature about one-half degree Fahrenheit, the temperature rise coming abruptly at the time of ovulation. During the first half of the menstrual cycle, the temperature fluctuates around 97.6 to 98.0 degree Fahrenheit, then, in a space of 1-2 days, the temperature undergoes a rather steep rise of about 0.9 degree Fahrenheit, to around 98.6 to 99.0 degree Fahrenheit. It remains at this higher level until the next menstrual bleeding. What is important is that, on average, ovulation occurs 1-2 days before the steep rise in temperature.

Keeping in mind this temperature rise, temperature sensors are selected to accurately detect this small change. Two metal-oxide thermistors, 30$a$ and 30$b$ are selected and adjusted in two of the holes around the probe to detect the small range of temperature during the menstrual cycle. Metal-oxide thermistors are formed by mixing together powdered metal oxides, molding them into desired shapes and forming a semiconducting, ceramic-like material whose resistance changes rapidly with temperature. Their response is highly dependent on the oxide mixtures used, and on the manufacturing process. Thermistors used for temperature measurement generally have a negative temperature coefficient. They are narrow range, highly sensitive, nonlinear devices whose resistance decrease with increasing temperature.

Thermistors are offered in numerous configurations. Styles include very small beads, discs ranging from under 0.1 inch to 1 inch or so in diameter, and washers and rods of various dimensions. The thermistor may be coated with epoxy, dipped in glass or otherwise coated, or left unpackaged. The manufacture of precision thermistors begins with careful control and measurement of the slope and stability of each oxide mix. The thermistors are pressed sintered, and metallized, then ground to a precise resistance at a tightly controlled temperature. By proper manufacturing control, precision from $\pm 0.05$ to $\pm 0.2$ degree centigrade is attainable. For basal body temperature detection, the thermistors 30$a$ and 30$b$ can be efficiently calibrated and the corresponding decreased resistance at ovulation can be detected. With respect to the circuitry for detecting temperature, it preferably includes a basic resistance bridge including a thermistor and three fixed resistors. The bridge's output voltage increases with temperature, i.e., thermistors resistance decrease with an increase in temperature. The bridge's output voltage is conditioned and converted into digital data for interface with the microprocessor. Information on interfacing and software development is explained later below.

The postulated mechanism of ovulation has as its initiating cause a large quantity of luteinizing hormone LH secreted by the anterior pituitary gland. The luteinizing hormone in turn causes rapid secretion of the follicular steroid containing a small amount of progesterone. Within a few hours, two events occur, both of which are necessary for ovulation: 1) the capsule of follicle begins to form proteolytic enzymes that cause weakening of the wall, swelling of the entire follicle and the degeneration of stigma and the 2) growth of new blood vessels into the follicle wall, and local hormones are secreted in the follicular tissues causing vasodilation. These two effects contribute to follicle swelling, causing follicle rupture with evagination of the ovum.

Approximately two days before ovulation, the rate of secretion of LH by the anterior pituitary gland increases markedly, rising six-to-ten fold and peaking about 18 hours before ovulation. Chemically, the hormones of the anterior pituitary are proteins, and the luteinizing hormone is categorized as proteins. The sensing of this hormone in the detection of the ovulation is extremely critical. As ultrasound is absorbed by the proteins, the technique of ultrasound transmission and reception at the housing site is used in the detection process of this hormone.

Ultrasound of high frequency is transmitted through the holes at sensors 28a and 28b sites of the probe. On transmission, ultrasound crosses LH protein layers, interacts with vaginal soft tissues, reflects from the surface of soft tissues, crosses again the LH protein layers on its return path, and is collected by the ultrasound receiver at the holes of the housing. A small size piezoelectric crystal acts as a transmitter and receiver. The presence of LH proteins is determined by the receiving amplitudes of the ultrasound reflected signal. If the reflected signal is weak, it suggests that ultrasound has been absorbed by LH proteins when ultrasound crossed the layers twice on its transmission and reception paths.

A threshold of the ultrasound reflected signal is determined to suggest whether LH hormones are present or not. If the reflected signal is smaller than the threshold value, then it indicates that the LH hormones are present. There are two ultrasound piezoelectric crystals fixed at sensors 28a and 28b. Caution must be taken to ensure that air is not trapped between the probe and the vaginal soft tissues, as ultrasound is fully reflected from the air interface before ever reaching LH layers. The processing of ultrasound data (called LH data) is discussed below in the microprocessor section.

Ovulation in a woman who has a normal 28-day female sexual cycle, occurs only 14 days after the onset of menstruation. Shortly before ovulation, the protruding outer wall of the follicle swells rapidly, and a small area in the center of the capsule, called the stigma, protrudes like a nipple. In another half hour or so, fluid begins to ooze from the follicle through the stigma. About two minutes later, as the follicle becomes smaller because of loss of fluid, the stigma ruptures widely, and a more viscous fluid that has occupied the central portion of the follicle is evaginated outward into the abdomen. This viscous fluid carries with it the ovum surrounded by several thousand small granulosa cells called corona radiata.

Once the follicle ruptures, the viscous fluid and mucous collects at the mouth of the cervix. Apart from the LH secretion (that is needed for the follicle to progress to the stage of ovulation), the alkalinity of the fluid and the density of the mucous are determining factors of ovulation. Most mucous collects at the mouth of the cervix, whereas LH secretion is around the vaginal canal. The alkalinity of the fluid is determined by the pH electrodes and the mucous density is determined by a pressure sensor 32, faced towards the mouth of the cervix.

In sensor 32, a thin diaphragm senses pressure due to a build up of mucous at the mouth of the cervix. This pressure is converted into an electrical signal. The larger the mucous density, the more pressure on the diaphragm, (i.e. increased stretching of the diaphragm) thus increased resistance across the diaphragm pressure sensor. The sensor 32 is attached at the tip of the housing. The sensor faces the mouth of the cervix when the housing is inserted in the vagina. The sensor 32 is fixed in such a way that it does not realize any pressure coming onto the thin diaphragm from the walls and the mouth of the vagina, except when sufficient mucous builds up due to ovulation.

Figure 4:
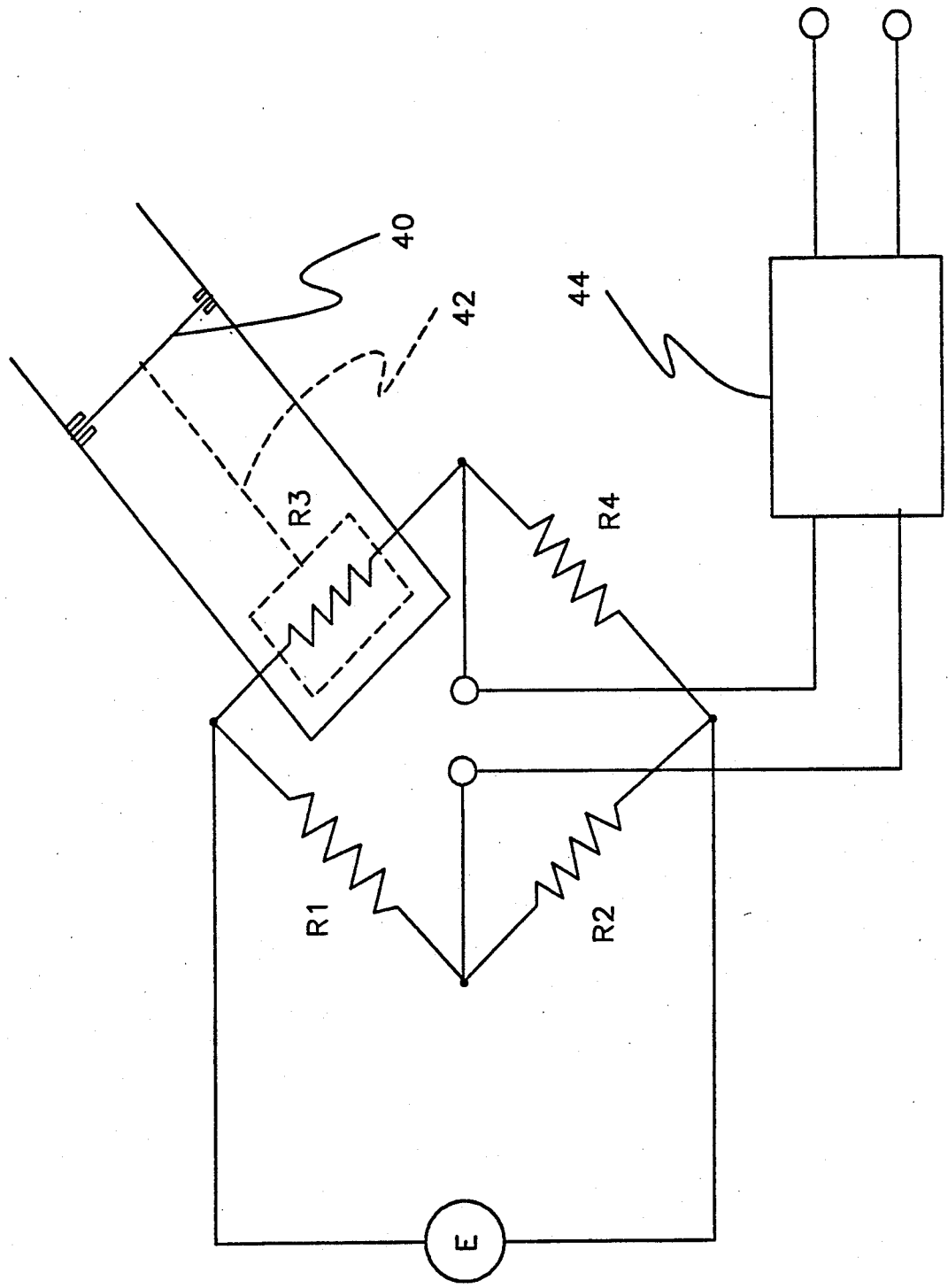
FIG. 4 is a schematic of the luteinizing hormone sensor.

A simple pressure sensor with a sealed diaphragm is shown in FIG. 4. As pressure builds up on the diaphragm 40, resistance increases and the output voltage also increases across the bridge network. A threshold value is determined for the mucous pressure and is compared with the instantaneous mucous pressure when the data is collected for determining ovulation. The sensor also includes a coupler 42 and a signal conditioner 44.

The pH of a solution is a measure of the acidity or alkalinity of the solution. To understand pH one must first understand the law of mass action as it applies to water and aqueous solutions. The pH represents the chemical potential energy stored in an acid or base. The pH of a solution is measured as an electrical potential (i.e. voltage using specifically designed electrodes, the potential being zero at a pH of 7). This potential represents the activity, or potential for doing work, of the dissociated H+ or OH− ions. For a given concentration, it represents the degree of ionization or dissociation of the dissolved acid or base molecules. A highly dissociated acid or base has a higher potential and thus a pH farther from 7 than a weak, slightly dissociated substance.

In determining the pH of the secretion in the vagina due to ovulation, two pH electrodes, 34a and 34b, are placed in proper locations around the housing as sensors. These are typical glass pH electrodes. The tip is the membrane, a very thin section blown using a specially formulated glass. Inside the body of the sensor is an electrode, generally made of silver wire coated with silver chloride, and chloride solution, generally chemically buffered to a pH of 7. Similar to the threshold values of basal body temperature, LH, and the mucous pressure, a threshold value of pH is determined for the ovulating fluid and the secretion. The processing of pH data is explained below.

The monitor 10 has as its power source 36 preferably a pair of AA size batteries. The relatively infrequent use and negligible power consumption thereby permits the unit to enjoy an extended shelf life before the batteries no longer provide sufficient power for operation of the device. Due to the relatively lengthy life of the monitor, it is possible to, in effect, permanently seal the base 14 to the tube 12, such that after an extended period of time, i.e. two years, the device may be discarded and a new one purchased. In the alternative, the tube can be made so as to permit the removal of the used cells, and the insertion of fresh ones. The cost for such a monitor would be relatively inexpensive, due to the electronic technology involved and mass production.

Figure 5A:
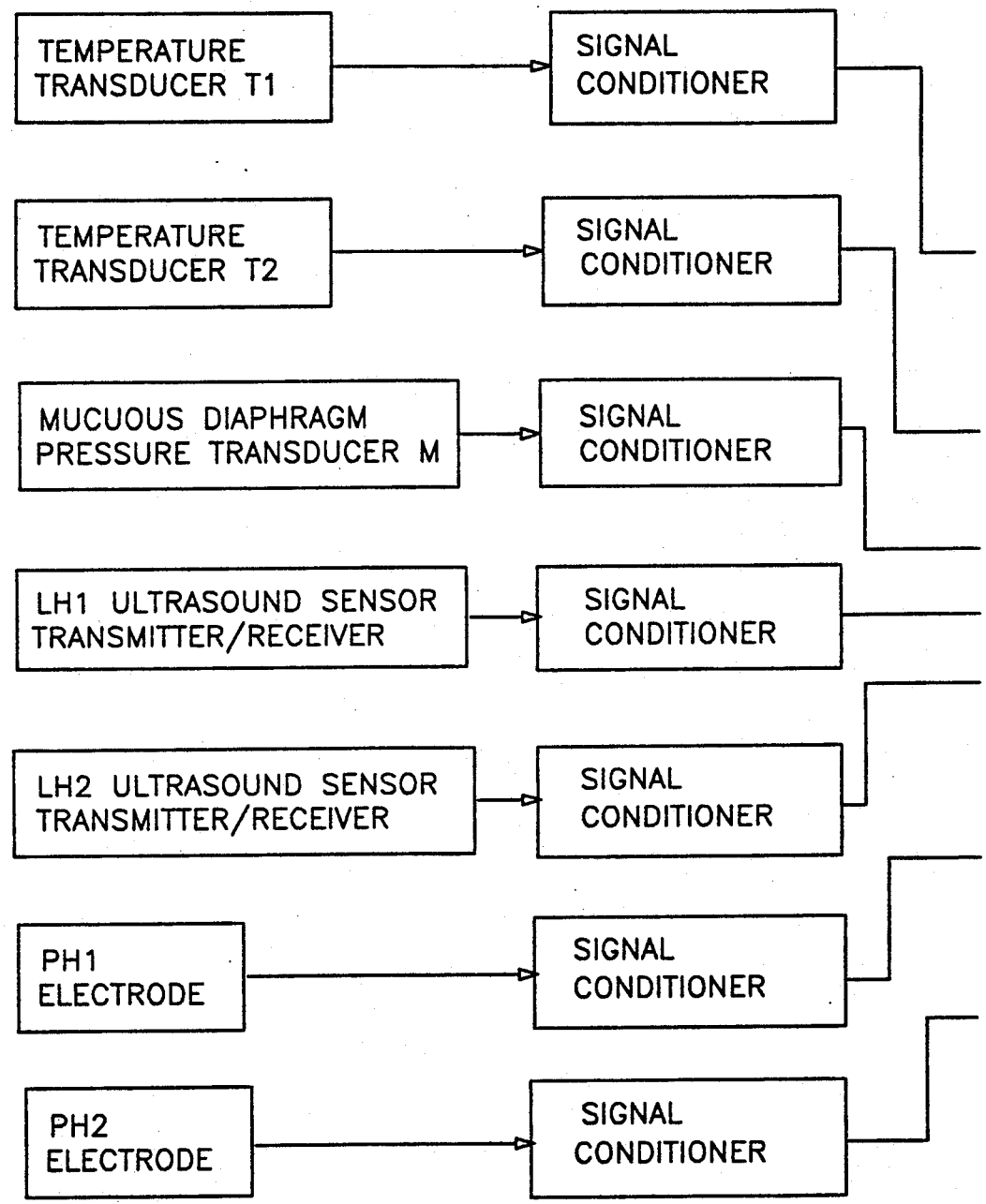
FIGS. 5 (A-C) are flow charts disclosing how the data is collected, multiplexed, digitized, and interfaced with the microprocessor.
Figure 5C:
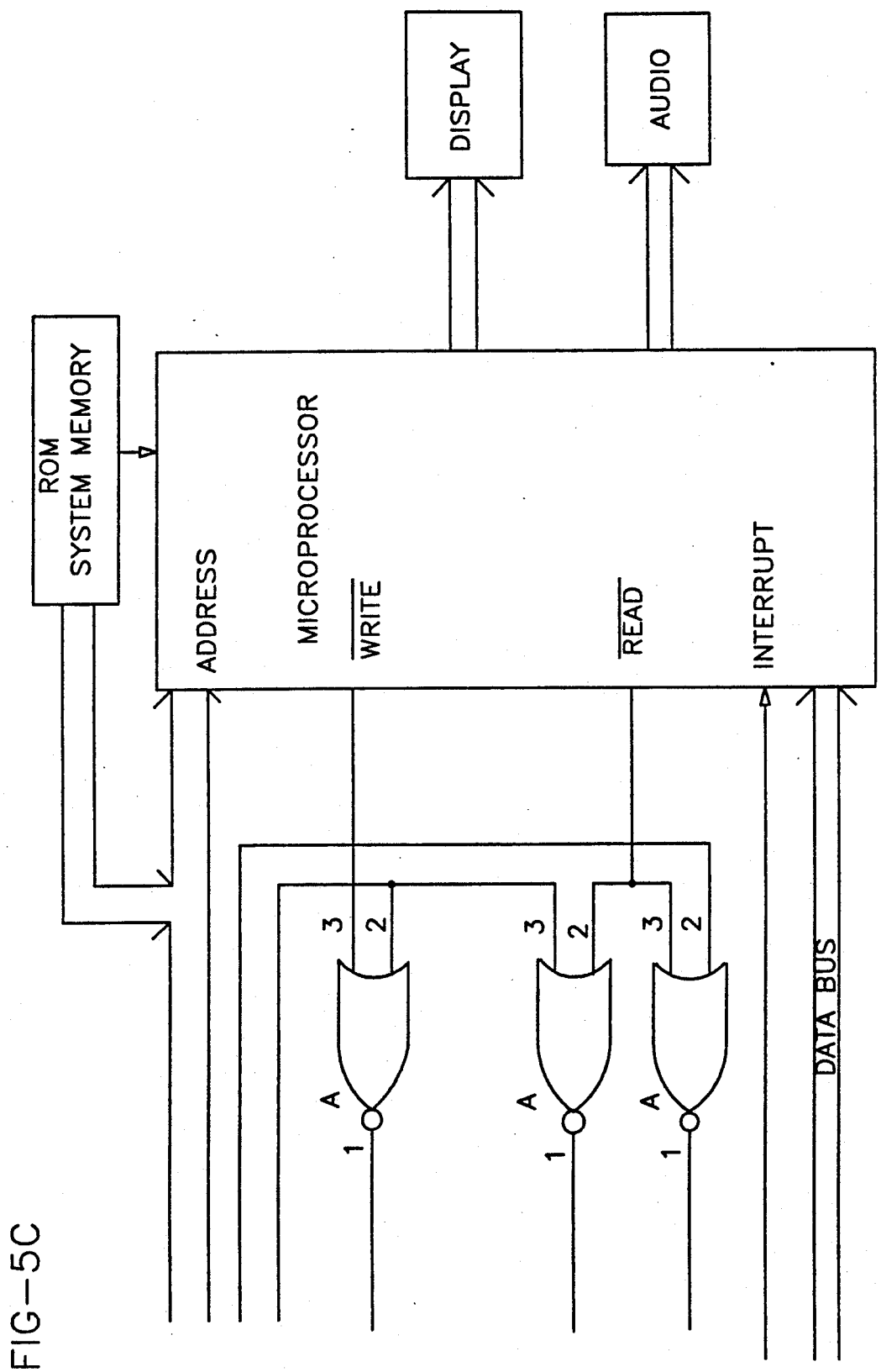

As shown in FIG. 3, the device has a housing with seven sensors, electronic circuits, microprocessor, battery pack, audio unit, and light-emitting diode. The sensors are fixed and glued in holes around the housing. FIG. 5 shows in detail how the analog data from the sensors are collected, multiplexed, digitized, and interfaced with the microprocessor. The outputs of all sensors and transducers are electrical analog signals. Most of the signals are in millivolts. Except for the LH sensors, the temperature, mucous pressure, and pH sensors have values converted into electrical signals. In the case of the LH sensors, piezoelectrical crystals are triggered by an oscillator for ultrasound transmission. Upon the reception of the reflected ultrasound, the echoes are processed to generate a specific voltage level.

Each sensor output is then signal conditioned for amplification and filtering, being addressed as channel 1 to 7 in an analog multiplexer or switch. When the microprocessor is ready to sample one of the channels, it instructs the channel through an address decoder to the analog switch. The channel analog signal is digitized in an A/D converter after it is sampled and held constant at a voltage level. The digitized data for each sample is read into the microprocessor and processed with the steps and instructions stored in read only memory. Once the decision of determining the ovulation is reached, the output devices, speaker and the light emitting diode, are activated by the microprocessor.

In actual use, a woman would insert the electronic ovulation monitor 10 into her vagina, wherein sensing means 16 would permit the transmission of information on mucous density, basal temperature, pH level and LH level to the processing means. If those values were to indicate the presence of a viable egg, then the visual display and audible component would immediately notify the user that a viable egg is present by signaling. If no such indication is made, the user could conclude that no egg is present.

While it is expected that the device of this invention will find use with humans, the device of this invention could be used with other animals to detect the presence of a viable egg. In such cases, the values for temperature, pH, LH and mucous density would be programmed with the particular type of animal in mind.

Figure 6C:
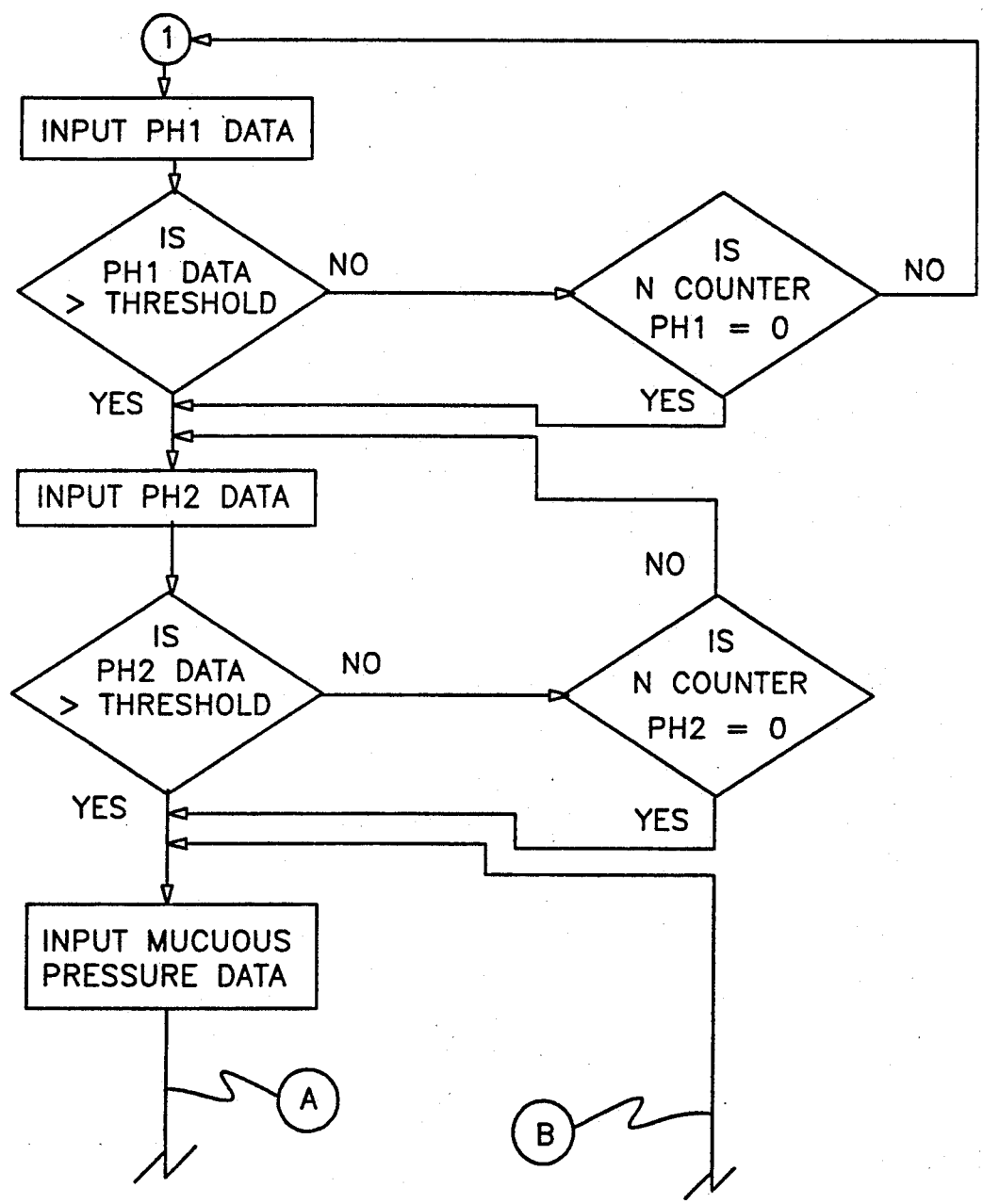
FIGS. 6 (A and D) are flow charts for the software of the microprocessor.
Figure 6D:
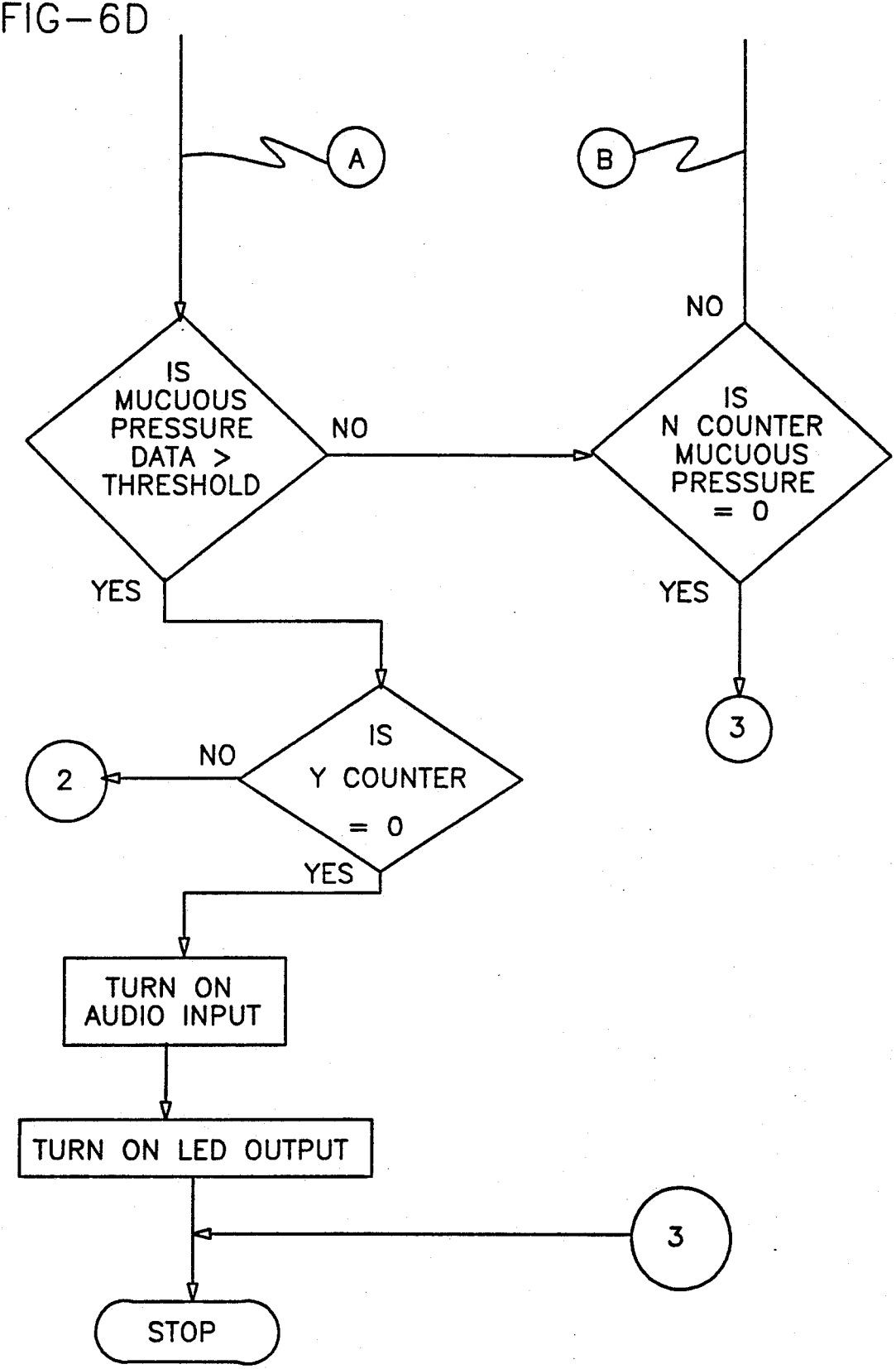

The decision of ovulation is not simple. Using this device permits the basal body temperature, LH level, pH level, and mucous density data to be monitored, compared with thresholds, and updated before the decision on ovulation is made. When basal body temperature is high, LH level is elevated, pH level is high, and mucous pressure is large, ovulation is occurring. As can be seen in FIG. 6, the flow chart for the software has a Y COUNTER and several N COUNTERS. If all four parameters are elevated, the Y COUNTER decides to check one or more times whether the parameters are still elevated before the speaker and the LED are activated. Similarly, the N COUNTER decides to check one or more times whether the parameter is still under threshold and not sufficiently elevated before giving up.

While the form of apparatus herein described constitutes a preferred embodiment of this invention, it is to be understood that the invention is not limited to this precise form of apparatus, and that changes may be made therein without departing from the scope of the invention which is defined in the appended claims. For example, while preferably the invention is used to signal the presence of a viable egg, since sperm may live 48 to 72 hours outside a male, the microprocessor chip could be adjusted to indicated that pre-ovulation conditions exist, such that any sperm subsequently introduced into the female would find a viable egg present within 48 hours. In such instance, the determination would be contraindicative of conditions favorable to the presence of a viable egg. As such the signaling could be either by an audible or visual component, e.g. a light emitting diode. Also, the processing means includes comparison of the values with data associated with conditions favorable to the presence of a viable egg.

What is claimed is:

1. An electronic ovulation monitor comprising a rod-shaped housing, means for sensing and measuring four values, namely basal body temperature, mucous density, pH level and LH level, means for processing said values to determine if each value is contraindicative of the presence of a viable egg, and means for immediately signaling the presence of a viable egg.

2. A monitor as claimed in claim 1 wherein said means for immediately signaling the presence of a viable egg comprises a visual component.

3. A monitor as claimed in claim 2 wherein said means for immediately signaling the presence of a viable egg comprises an audible component.

4. A monitor as claimed in claim 3 wherein said visual component comprises a light emitting diode.

5. A monitor as claimed in claim 1 wherein said means for processing said values includes comparison of said values with data associated with the presence of a viable egg.

6. An electronic ovulation monitor comprising means for sensing and measuring values, namely basal body temperature, mucous density, pH level and LH level, means for processing said values to determine if each value is contraindicative of the presence of a viable egg, said means for processing said values including comparison of said values with data associated with the presence of a viable egg, and said monitor comprising means for immediately signaling the presence of a viable egg after said values are processed, said means for immediately signaling the presence of a viable egg comprising a visual component.

7. A monitor as claimed in claim 6 wherein said means for immediately signaling the presence of a viable egg comprises an audible component.

8. A monitor as claimed in claim 7 wherein said visual component comprises a light emitting diode.

9. An electronic ovulation monitor comprising a rod-shaped housing, means for sensing and measuring four values, namely basal body temperature, mucous density, pH level and LH level, means for processing said values to determine if each value is contraindicative of the presence of conditions favorable to the presence of a viable egg, and means for immediately signaling conditions favorable to the presence of a viable egg.

10. A monitor as claimed in claim 9 wherein said means for immediately signaling conditions favorable to the presence of a viable egg comprises a visual component.

11. A monitor as claimed in claim 10 wherein said means for immediately signaling conditions favorable to the presence of a viable egg comprises an audible component.

12. A monitor as claimed in claim 11 wherein said visual component comprises a light emitting diode.

13. A monitor as claimed in claim 9 wherein said means for processing said values includes comparison of said values with data associated with conditions favorable to the presence of a viable egg.

* * * * *